(12) United States Patent
Fankhauser et al.

(10) Patent No.: US 7,494,491 B2
(45) Date of Patent: Feb. 24, 2009

(54) DEVICE FOR IMPLANTING MARKING BODIES

(75) Inventors: Christoph Fankhauser, Solothurn (CH); René Von Burg, Bettlach (CH)

(73) Assignee: Mathys AG Bettlach, Bettlach (CH)

( * ) Notice: Subject to any disclaimer, the term of this patent is extended or adjusted under 35 U.S.C. 154(b) by 340 days.

(21) Appl. No.: 10/505,463

(22) PCT Filed: Mar. 12, 2003

(86) PCT No.: PCT/EP03/02567

§ 371 (c)(1),
(2), (4) Date: Apr. 8, 2005

(87) PCT Pub. No.: WO03/084419

PCT Pub. Date: Oct. 16, 2003

(65) Prior Publication Data

US 2005/0222609 A1    Oct. 6, 2005

(30) Foreign Application Priority Data

Apr. 10, 2002    (DE) ................................ 102 15 751

(51) Int. Cl.
*A61B 17/58* (2006.01)
(52) U.S. Cl. ...................................................... 606/99
(58) Field of Classification Search .................. 606/99, 606/139, 142, 143, 104, 185–189, 206; 600/7, 600/414, 426, 407; 604/59, 62, 72, 73, 93.01, 604/130, 164.01, 164.12, 166.01, 181, 232; 81/57.23, 57.37; 128/899
See application file for complete search history.

(56) References Cited

U.S. PATENT DOCUMENTS

| 3,489,330 | A | * | 1/1970 | Mallina et al. | ................. 227/19 |
| 3,669,104 | A | * | 6/1972 | Wyatt et al. | ................... 604/61 |
| 4,241,861 | A | | 12/1980 | Fleischer | ..................... 227/135 |
| 4,583,670 | A | * | 4/1986 | Alvarado | ...................... 227/19 |
| 4,657,533 | A | * | 4/1987 | Oscarsson | ..................... 604/60 |

(Continued)

FOREIGN PATENT DOCUMENTS

DE            1766037            5/1971

(Continued)

OTHER PUBLICATIONS

International Search Report in PCT/EP03/02567 dated Jun. 4, 2003.

(Continued)

*Primary Examiner*—Eduardo C Robert
*Assistant Examiner*—Nicholas Woodall
(74) *Attorney, Agent, or Firm*—Marshall, Gerstein & Borun LLP

(57) ABSTRACT

A device for implanting marking bodies into a bone is provided in the form of forceps whereby comprising a medial forceps handle, a lateral forceps handle, a medial forceps limb, a lateral forceps limb, and a spring element. The spring element acts upon the medial forceps handle and upon the lateral forceps handle, and the medial forceps limb and the lateral forceps limb can be displaced parallel relative to one another by means of a four-bar linkage for ejecting the marking bodies. A magazine containing the marking bodies can be slid onto a magazine holding fixture situated on the lateral forceps limb.

16 Claims, 3 Drawing Sheets

U.S. PATENT DOCUMENTS

| | | | | |
|---|---|---|---|---|
| 4,827,493 A | * | 5/1989 | Parsons et al. | 378/119 |
| 5,221,036 A | * | 6/1993 | Takase | 227/19 |
| 5,351,871 A | * | 10/1994 | Bauer | 227/177.1 |
| 5,540,240 A | | 7/1996 | Bauer | 128/898 |
| 6,090,131 A | * | 7/2000 | Daley | 606/219 |
| 6,131,790 A | | 10/2000 | Piraka | 227/176.1 |
| 6,315,183 B1 | * | 11/2001 | Piraka | 227/176.1 |
| 6,551,338 B1 | * | 4/2003 | Chiu et al. | 606/186 |
| 6,689,121 B1 | * | 2/2004 | Cafferata | 604/891.1 |

FOREIGN PATENT DOCUMENTS

| | | |
|---|---|---|
| DE | 297 17 890 U1 | 3/1999 |
| EP | 146 699 A1 | 7/1985 |
| FR | 1187573 | 9/1959 |
| GB | 1227831 | 4/1971 |

OTHER PUBLICATIONS

International Preliminary Examination Report in PCT/EP03/02567 dated Jul. 16, 2004.

* cited by examiner

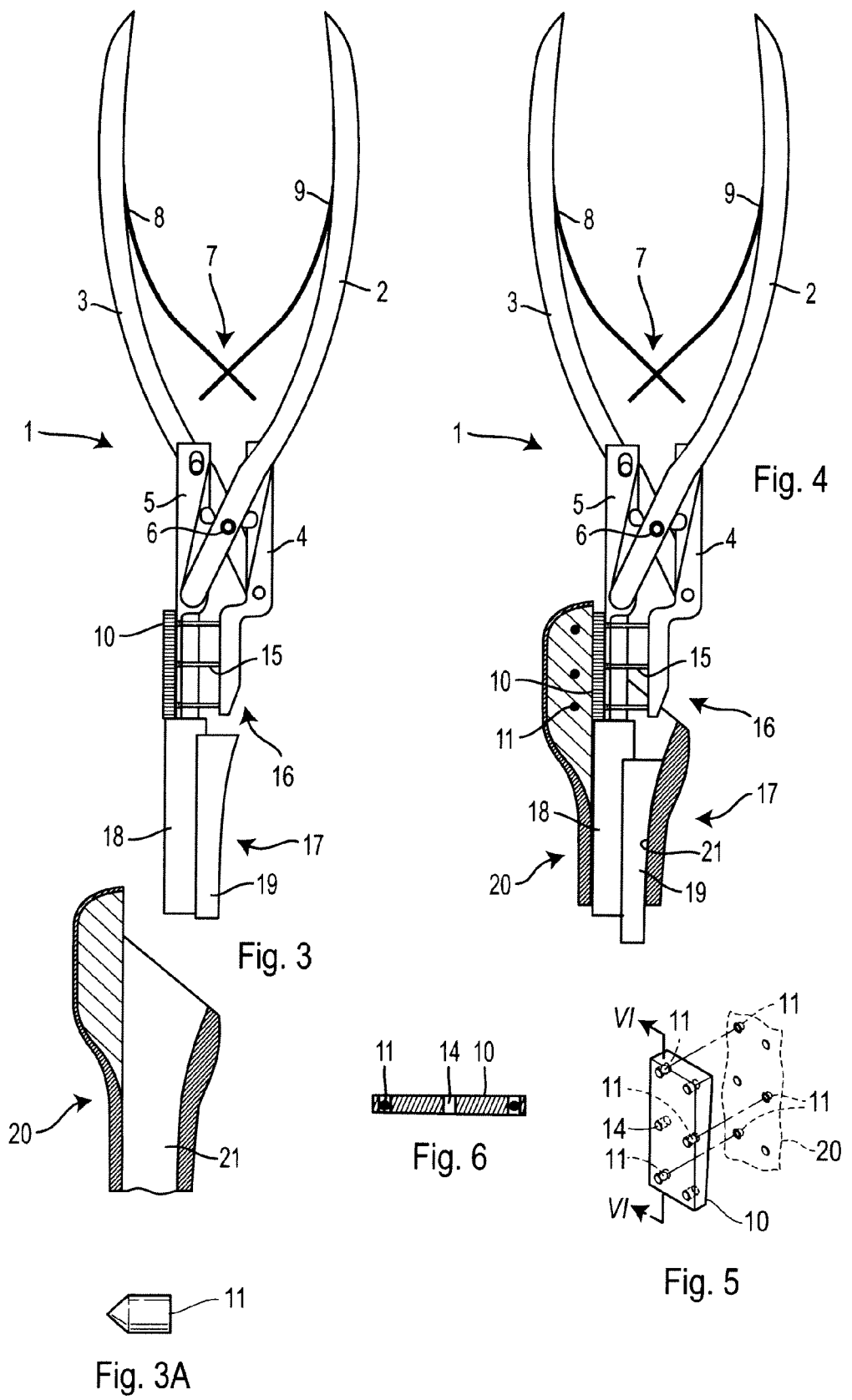

DEVICE FOR IMPLANTING MARKING BODIES

This is the U.S. national phase of International Application No. PCT/EP03/02567 filed Mar. 12, 2003, the entire disclosure of which is incorporated herein by reference.

BACKGROUND

1. Field of the Disclosure

The disclosure relates to a device for the implantation of marking bodies in a human or animal bone and a magazine with marking bodies for this device.

2. Related Technology

Marking bodies, preferably metallic balls, can be introduced into the human or animal skeleton to allow a quantification of the migration of implants, in particular joint prostheses, especially replacement knee joints and hip joints. For this purpose, a number of devices are already known, which operate in a similar manner to an injection syringe, one marking ball being placed by hand into a cannula of the injection syringe for each use and then introduced into the bone.

The particular disadvantage with the known devices is that, during the operation, the marking balls have to be individually loaded or unloaded manually by the operator using tweezers or a similar instrument, which prolongs the operating time.

It is also disadvantageous that, although the marking balls can be packed in a sterile manner before loading, they become un-sterile after loading.

Another device for the implantation of marking bodies in a bone, which comprises a magazine for the marking bodies and an ejector mechanism for the marking bodies, is known from DE 297 17 890 U1. This device is designed in the form of a pistol. The magazine is designed as a revolving chamber and contains several marking bodies.

The disadvantage of this device is that the marking balls must be ejected and implanted one after the other, so that the spacing between marking balls is more or less random, and it is therefore not possible to ensure a reproducible spacing between the individual marking balls.

SUMMARY

The disclosure provides a device, which allows a simple and rapid, simultaneous insertion of at least one, preferably several, preferably sterile marking bodies at a defined position relative to one another into the skeleton in order to quantify the migration of implant components relative to the bone, and a magazine with marking bodies for this device.

The device is designed in the form of forceps, and including medial and lateral forceps handles and medial and lateral forceps limbs wherein a magazine with at least one marking body can be attached to a magazine retained on one of the forceps limbs.

The disclosure also provides a magazine useful in the device;

The device is explained in greater detail below with reference to a preferred exemplary embodiment on the basis of the drawings. The drawings are as follows:

BRIEF DESCRIPTION OF THE DRAWINGS

FIG. 3 shows a lateral view of the exemplary embodiment of the device according to the disclosure with the magazine fitted and a distal guide attached;

FIG. 3A shows a lateral view of one embodiment of marking body useful in the invention.

FIG. 4 shows a lateral view of the exemplary embodiment of the device according to the disclosure with the magazine fitted and the attached distal guide inserted into the bone cavity;

FIG. 5 shows an isometric view of an exemplary embodiment of the magazine to be used with the device according to the invention, with the already pre-loaded marking balls;

FIG. 6 shows a cross-section through the magazine shown in FIG. 5 along the line marked VI-VI.

DETAILED DESCRIPTION

Figure 1:
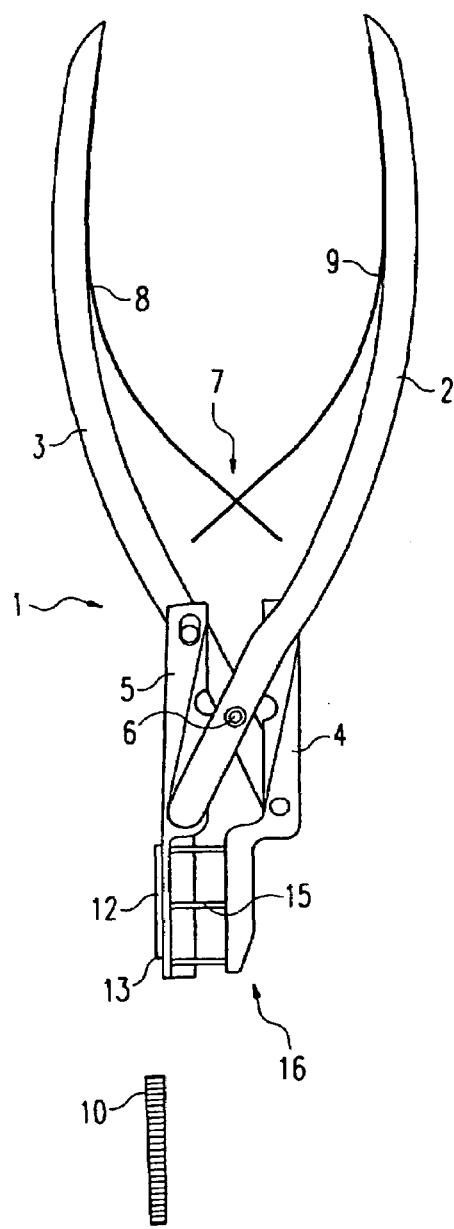
FIG. 1 shows a lateral view of an exemplary embodiment of the device according to the disclosure.

FIG. 1 shows a lateral view of an exemplary embodiment of a device 1, which comprises a medial forceps handle 2, a lateral forceps handle 3, a medial forceps limb 4, and a lateral forceps limb 5. The forceps handles 2 and 3 and the forceps limbs 4 and 5 are connected to one another via a four-lever articulated joint 6. When the forceps handles 2 and 3 are activated, the two forceps limbs 4, 5 are displaced parallel to one another.

A spring element 7 which, in the exemplary embodiment consists of two complementary plate springs 8, 9 attached to each forceps handle 2, 3, is deformed in a resilient manner when the forceps handles 2, 3 are activated. When the forceps handles 2 and 3 are released, the spring element 7 acts to push the forceps handles 2, 3 apart again and the two forceps limbs 4, 5 accordingly move away from one another.

Figures 1, 1A:
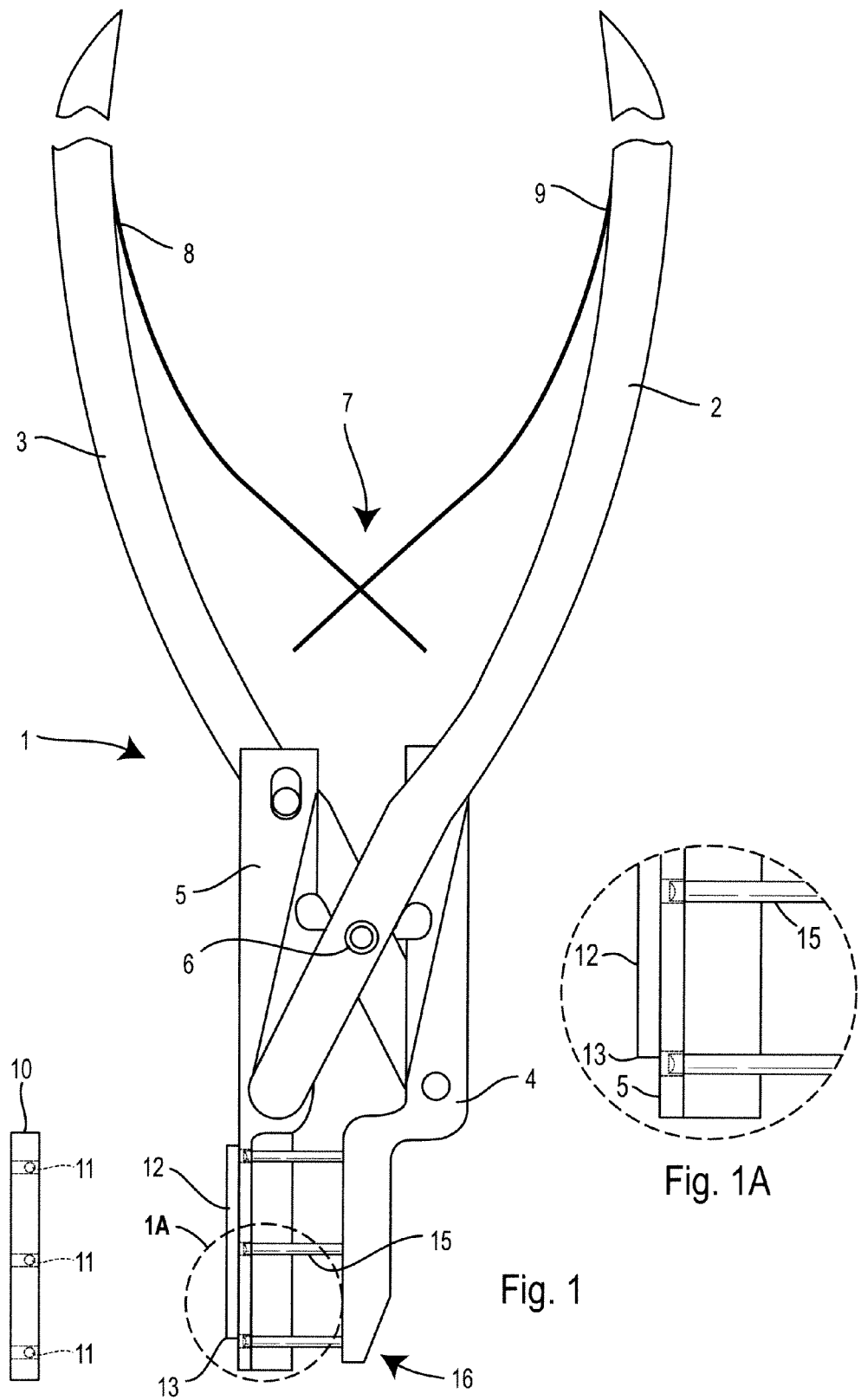
FIG. 1a shows an enlarged view of a portion of the embodiment of the device of FIG. 1.

A magazine 10, which contains marking bodies 11 in a given arrangement, is attached to a magazine retainer 12, in the exemplary embodiment, in the form of a magazine guide attached to the lateral side of the lateral forceps arm 5, and, in the exemplary embodiment, pushed up to a stop 13, so that boreholes 14 of the magazine 10 are in mutual alignment with pins 15. The pins 15 are attached to the medial forceps limb 4 and point towards the lateral forceps limb 5, on which the magazine 10 is attached by plug-on or push-on attachment. The pins 15 provide a concave tip (best seen in FIG. 1A) to ensure that they do not slip sideways on the marking bodies 11, inserting them from the magazine 10 into a bone 20 in a defined position relative to one another, as described below.

Figure 2:
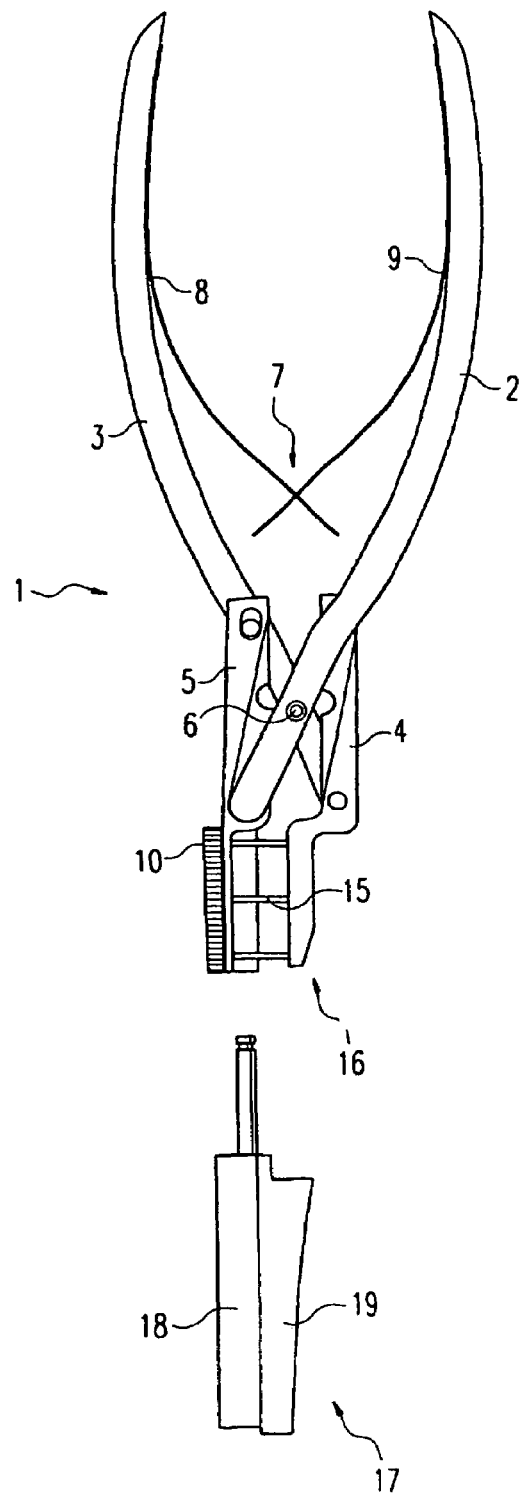
FIG. 2 shows a lateral view of the exemplary embodiment of the device according to the disclosure with the magazine fitted.

In the same view as FIG. 1, FIG. 2 shows the device 1 with the magazine fitted and with a guide 17, which can be plugged onto a distal end of the lateral forceps limb 5. In this context, the guide 17 comprises a lateral guide 18 and a medial guide 19, which can be displaced relative to one another.

FIG. 3 shows the lateral guide 18 already fitted to the lateral forceps limb 5. The medial guide 19, which is fixed to the lateral guide 18 with an attachment device, which is not presented in greater detail here, can be displaced relative to the lateral guide 18. Accordingly, the longitudinal position of the magazine 10 and therefore also the position of the marking bodies 11 relative to the bone 20 can be selected FIG. 3A shows a marking body 11 having a conical tip.

FIG. 4 shows how the device 1 is inserted into a cavity 21 of the bone 20. In the exemplary embodiment, the bone is a femur 21, into the proximal end of which a cemented or uncemented replacement hip joint is to be inserted after referencing the bone by means of the device 1 according to the invention. In this diagram, by comparison with FIG. 3, the position of the medial guide 19 is displaced in the distal direction, so that the depth of insertion of the device 1 is limited. With the lateral guide 18 and the medial guide 19 in the position shown in FIG. 3, the device 1 could be pushed deeper into the cavity 21; with a further distal displacement of the medial guide 19 relative to the lateral guide 18, the depth of insertion would be reduced.

The diameter of the marking bodies 11, preferably designed as marking balls, is typically 0.5 mm to 2.0 mm. With cylindrical marking elements 11, these may be 3 mm to 6 mm long, and then preferably have a conical tip with a conical angle between 30° and 90°. Bio-compatible materials such as tantalum, pure titanium, titanium alloys, stainless steel, calcium phosphate ceramics, technical ceramics, resorbable ceramics, polymers or composites, which, through x-ray absorption, produce a clear contrast on the x-ray image relative to the surrounding bone 20, are suitable materials for the marking bodies 11.

After positioning the device as required in the cavity 21 with the assistance of the guide 17, the device 1 for the insertion of the marking bodies 11 is activated by pressing together the medial forceps handle 2 and the lateral forceps handle 3 against the force of the spring element 7. As a result of the four-lever articulated joint 6, the medial forceps limb 4 is moved in a parallel manner towards the lateral forceps limb 5 until the pins 15 are in contact with the marking bodies 11 arranged in the magazine. As a result of the continued squeezing together of the device 1, the pins 15 press the marking bodies 11 through the boreholes 14 into the tissue structure of the bone 20

At least two marking are advantageously arranged in at least two rows in a non-collinear manner, thereby allowing the possibility of two-dimensional marking.

In this context, the marking bodies are preferably spherical or cylindrical with a conical tip and are formed of material, which, through x-ray absorption, shows an adequately high contrast by comparison with the surrounding bone tissue.

Furthermore, it is advantageous that pins engage in the magazine in such a manner that the marking bodies are pressed simply and simultaneously into the bone tissue up to a predetermined depth.

A guide advantageously allows a limitation and regulation of the depth of insertion of the device into a bone cavity.

FIG. 5 shows a plan view of a magazine 10 to be used with the device 1 according to the invention. In the left-hand diagram, the magazine 10 is empty; while in the right-hand diagram, the magazine is loaded with three marking bodies 11. After insertion into the bone, preferably with pins 15 of identical length, the marking bodies 11 from the magazine 10 are arranged in such a manner that they form a bone-reference system, preferably a plane, when three marking bodies 11 are used. As a result, they provide reliable information about the setting movement (migration) of implant components with reference to the surrounding bone. In this context, the pre-loaded magazine 10 is preferably packed in a sterile manner and can be fitted to the device 1 in a sterile manner.

FIG. 6 shows a cross-section of the magazine 10 presented in FIG. 5 along the line VI-VI in FIG. 5. The marking bodies 11, which ate spherical in this exemplary embodiment, are arranged in the boreholes 14. To accommodate the angle of the bone 20, the magazine is designed in this context to be slightly trapezoidal with the narrow side in the distal direction. However, depending on requirements, general four-sided or rectangular profiles may also be used.

The invention claimed is:

1. Device for the implantation of at least two marking bodies in a bone, wherein the device is designed in the form of forceps and comprises a medial forceps handle, a lateral forceps handle, a medial forceps limb, a lateral forceps limb, and a magazine with the at least two marking bodies attached to a magazine retainer on one of the forceps limbs, wherein the magazine defines boreholes and the marking bodies are arranged in said boreholes and wherein the magazine retainer is provided on the lateral forceps limbs and pins, which extend in a direction towards the lateral forceps limb, are arranged on the medial forceps limb, and the device further comprises a guide attached to the distal end of the lateral forceps limb, the guide comprising a lateral guide component and a medial guide component.

2. Device according to claim 1, comprising a spring element acting on the medial forceps handle and the lateral forceps handle, and a four-lever articulated joint displaces the medial forceps limb and the lateral forceps limb in a mutually parallel manner.

3. Device according to claim 2, wherein the spring element comprises two complementary plate springs arranged on the lateral forceps handle and the medial forceps handle.

4. Device according to claim 1, wherein the boreholes of the magazine are arranged in several rows.

5. Device according to claim 4, wherein the marking bodies are arranged in a non-collinear manner and/or span a plane.

6. Device according to claim 1, wherein the marking bodies are spherical.

7. Device according to claim 1, wherein the marking bodies are cylindrical.

8. Device according to claim 7, wherein the marking bodies define a conical tip with a conical angle between 30° and 60°.

9. Device according to claim 1, wherein the marking bodies comprise a material, which, through x-ray absorption, produces a contrast relative to the bone.

10. Device according to claim 1, wherein the pins are arranged in mutual alignment with the boreholes of the magazine.

11. Device according to claim 1, wherein the pins have a concave end face.

12. Device according to claim 1, wherein when the device is activated, the pins are pressed into the boreholes in such a manner that the marking bodies arranged in the boreholes are at the same time pressed out of the boreholes and into the bone.

13. Device according to claim 1, wherein the magazine with the loaded marking bodies is packed in a sterile manner before attachment to the device.

14. Device according to claim 1, wherein the magazine comprising a structurally-rigid, sterilizable material.

15. Device according to claim 1 wherein the medial guide component is arranged in a longitudinally displaceable manner relative to the lateral guide component.

16. Device according to claim 15, wherein the degree of displacement of the medial guide component relative to the lateral guide component determines the depth of penetration of the device into a cavity of the bone.

* * * * *